(12) United States Patent
Morningstar et al.

(10) Patent No.: US 8,192,352 B2
(45) Date of Patent: Jun. 5, 2012

(54) INSTRUMENT CONFIGURED TO PREPARE A PENIS FOR IMPLANTATION OF A PENILE PROSTHETIC

(75) Inventors: Randy L. Morningstar, Brooklyn Park, MN (US); Donald Wolf, Vadnais Heights, MN (US)

(73) Assignee: Coloplast A/S, Humlebaek (DK)

( * ) Notice: Subject to any disclaimer, the term of this patent is extended or adjusted under 35 U.S.C. 154(b) by 34 days.

(21) Appl. No.: 12/832,998

(22) Filed: Jul. 9, 2010

(65) Prior Publication Data

US 2011/0144428 A1 Jun. 16, 2011

(30) Foreign Application Priority Data

Dec. 15, 2009 (DK) ................................. 2009 70276

(51) Int. Cl.
*A61F 5/00* (2006.01)
(52) U.S. Cl. ........................................................ 600/40
(58) Field of Classification Search .............. 600/38–41; 128/897, 898; 606/191, 192
See application file for complete search history.

(56) References Cited

U.S. PATENT DOCUMENTS

| 3,196,876 A * | 7/1965 | Miller ............................ 606/191 |
| 4,244,370 A | 1/1981 | Furlow et al. |
| 4,350,151 A | 9/1982 | Scott |
| 4,396,021 A | 8/1983 | Baumgartner |
| 4,705,041 A * | 11/1987 | Kim ............................... 606/108 |
| 5,342,384 A * | 8/1994 | Sugarbaker .................... 606/191 |
| 5,588,965 A | 12/1996 | Burton et al. |
| 5,686,729 A | 11/1997 | Bittar et al. |
| 6,102,929 A | 8/2000 | Conway et al. |
| 6,808,489 B2 | 10/2004 | George et al. |
| 6,916,330 B2 | 7/2005 | Simonson |
| 7,922,647 B2 * | 4/2011 | Slattery et al. .................. 600/25 |
| 7,938,842 B1 * | 5/2011 | Chin .............................. 606/190 |
| 2005/0004593 A1 * | 1/2005 | Simonson ...................... 606/191 |

FOREIGN PATENT DOCUMENTS

| WO | 02102230 | 12/2002 |
| WO | 03011970 | 2/2003 |
| WO | 2008/008547 | 1/2008 |

OTHER PUBLICATIONS

Office Action mailed on Mar. 4, 2011 in U.S. Appl. No. 12/639,069. No Office Action is provided since this reference is stored on the Office IFW.
International Search Report dated Mar. 8, 2011 in corresponding application No. PCT/DK2010/050338.

* cited by examiner

*Primary Examiner* — Samuel Gilbert
(74) *Attorney, Agent, or Firm* — Coloplast Corp., Coloplast A/S; Daniel G. Chapik; Nicholas R. Baumann (57) ABSTRACT

An instrument configured to prepare a penis for implantation of a penile prosthetic includes a shaft extending between a distal end and a proximal end, a plunger coupled to and movable relative to the shaft, and a dilation head coupled to a distal end of the plunger and disposed around an exterior of the shaft. The dilation head is movable longitudinally along the shaft.

17 Claims, 10 Drawing Sheets

INSTRUMENT CONFIGURED TO PREPARE A PENIS FOR IMPLANTATION OF A PENILE PROSTHETIC

BACKGROUND

Implanted penile prostheses address erectile dysfunction in men.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Thereafter, a tool (e.g., a "Furlow" introducer) is inserted into each corpora cavernosum to measure a length of the penis distally and proximally from a "stay" suture or other stationary landmark located near the opening formed in the fascia. Subsequently, each corpora cavernosum is dilated with at least one separate dilation tool, and often multiple dilation tools. For example, each corpora cavernosum is dilated by introducing gradually larger stainless steel rods into the corpora cavernosum to form a recess in the penis that is sized to receive a cylinder of the penile prosthesis.

The above-described procedure has proven effective in the implantation of penile prostheses. However, practitioners have expressed a continuing desire for more efficient and cost effective tools and procedures for implanting penile prostheses.

SUMMARY

One aspect provides an instrument configured to prepare a penis for implantation of a penile prosthetic. The instrument includes a shaft extending between a distal end and a proximal end, a plunger coupled to and movable relative to the shaft, and a dilation head coupled to a distal end of the plunger and disposed around an exterior of the shaft. The dilation head is movable longitudinally along the shaft.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

Multiple different tools and instruments are employed in a typical penile prosthetic implantation procedure to form a recess sized to receive the implant. In general, the fewer tools employed during a body implant procedure, the better.

Embodiments provide an instrument configured to prepare a penis for implantation of a penile prosthetic, where the instrument includes a dilation head that is movable longitudinally along a shaft of the instrument. The dilation head is movable to a proximal end of the shaft such that the shaft has a substantially uniform diameter that is unobstructed and thus configured for measuring a length of the corpora cavernosum. The dilation head is configured to be reversibly movable along the length of the shaft to "core out" and/or dilate the corpora cavernosum. Thus, a single one of the instruments as described herein provides improved dilation of the corpora with improved procedural efficiency by performing the tasks of the multiple different tools and instruments typically employed in a penile prosthetic implantation procedure.

Figure 1:
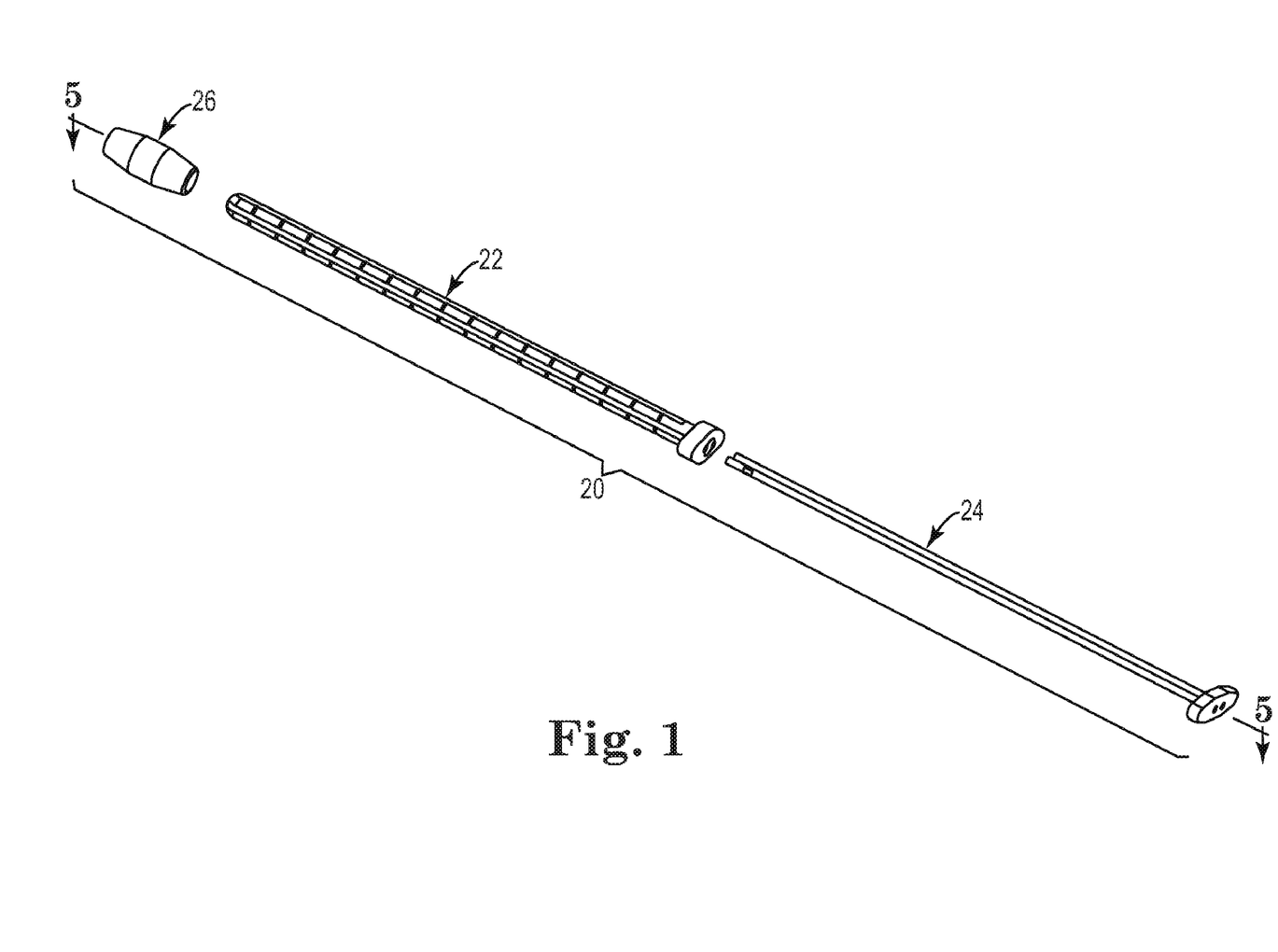
FIG. 1 is an exploded perspective view of one embodiment of an instrument that is configured to prepare a penis for implantation of a penile prosthetic.

FIG. 1 is an exploded perspective view of one embodiment of an instrument 20 that is configured to prepare a penis for implantation of a penile prosthetic. The instrument 20 includes a shaft 22, a plunger 24 that couples with and moves relative to the shaft 22, and a dilation head 26 that couples with the plunger 24. In one embodiment, the plunger 24 is inserted within the shaft 22 and the dilation head 26 is attached to the plunger 24 around the shaft 22. Longitudinal movement of the plunger 24 relative to the shaft 22 moves the dilation head 26 longitudinally along the shaft 22.

During use, as describe below, the plunger 24 is retracted proximally to draw the dilation head 26 toward a proximal end of the shaft 22, which configures the shaft 22 for unobstructed insertion into a corpora cavernosa of the penis to allow the shaft 22 to measure the length of the corpora cavernosa. After the length measurement is taken, and while the shaft 22 is inserted into the corpora cavernosa, the plunger 24 is pushed proximally into the shaft 22 to pass the dilation head 26 along the shaft 22 in the distal direction. The movement of the dilation head 26 along the shaft 22 dilates the tissue in the corpora cavernosa. The dilation head 26 is removable from the shaft 22 and the plunger to allow other differently sized dilation heads 26 to be attached to the plunger 24 for selective dilation of the corpora.

Figure 2A:
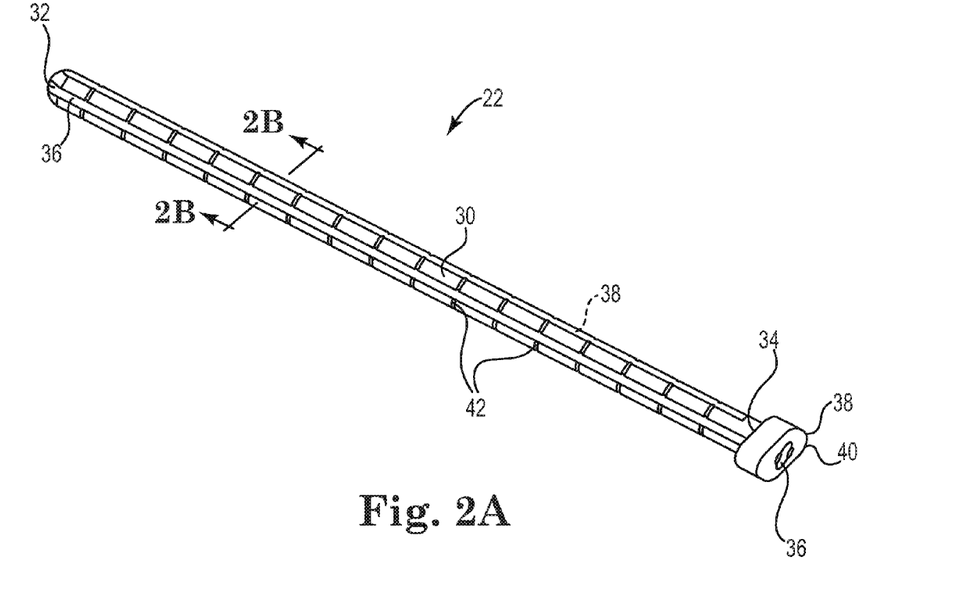
FIG. 2A is a perspective view of one embodiment of a shaft of the instrument illustrated in FIG. 1.
Figure 2B:
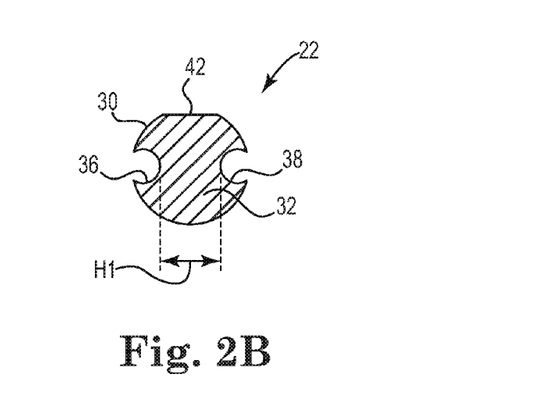
FIG. 2B is a cross-sectional view of the shaft illustrated in FIG. 2A.

FIG. 2A is a perspective view and FIG. 2B is a cross-sectional view of one embodiment of the shaft 22. In one embodiment, the shaft 22 has an exterior surface 30 that extends between a distal end 32 and a proximal end 34 and includes a first channel 36 and a second channel 38 that are formed in the exterior surface 30. The exterior surface 30 defines an outside diameter of the shaft 22, and in one embodiment the shaft 22 has a constant outside diameter that is suited for insertion into and measurement of a length of each corpora cavernosum. In one embodiment, the channels 36, 38 are open channels formed from a circular arc of greater than 180 degrees, where the first channel 36 is spaced a first distance H1 apart from the second channel 38.

In one embodiment, the shaft 22 is formed as a single monolithic shaft molded as a unit between the distal end 32 and the proximal end 34, and a handle 40 is attached to the proximal end 34 of the shaft 22.

In one embodiment, at least a portion of the exterior surface 30 of the shaft 22 is provided with indicia 42 placed at selected intervals, for example a series of markings spaced 1 cm apart, although other spacing is also acceptable. In one embodiment, the shaft 22 is fabricated from a circular rod to include the channels 36, 38 and a flat surface on which the indicia 42 are marked. In one embodiment, the indicia 42 are marked on the flat surface of the shaft 22 and over the exterior surface 30. Marking the indicia 42 on the flat surface minimizes the deleterious effects of glare, which can occur in the typically brightly-lighted operating rooms.

Figure 3A:
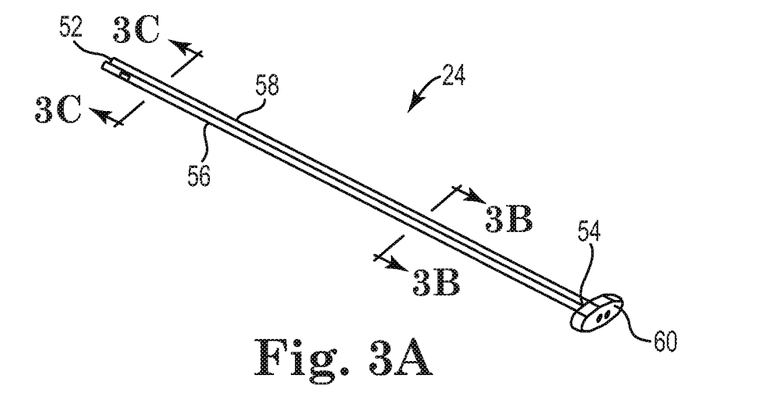
FIG. 3A is a perspective view of one embodiment of a plunger of the instrument that is insertable into the shaft illustrated in FIG. 2A.
Figure 3B:
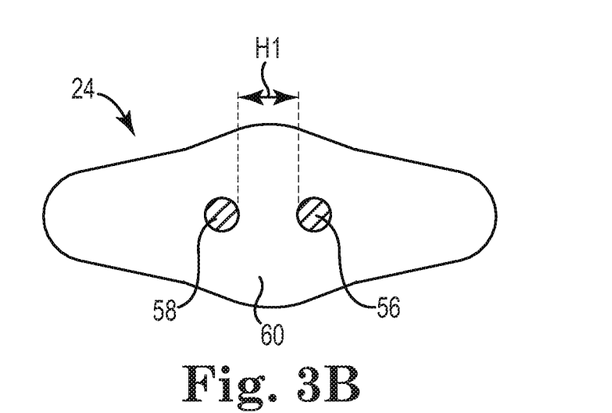
FIG. 3B is a cross-sectional view of a proximal end portion the plunger illustrated in FIG. 3A.
Figure 3C:
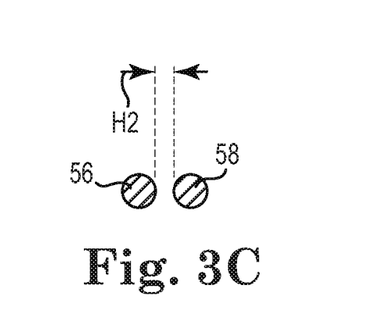
FIG. 3C is a cross-sectional view of a distal end portion of the plunger illustrated in FIG. 3A.

FIG. 3A is a perspective view and FIGS. 3B and 3C are cross-sectional views of one embodiment of the plunger 24. In one embodiment, the plunger 24 extends between a distal end 52 and a proximal end 54 and includes a first rod 56 and a second rod 58 spaced apart from the first rod 56, where the rods 56, 58 extend from a handle 60.

The rods 56, 58 are sized to slide within the channels 36, 38 (FIG. 2B). For example, the rods 56, 58 are formed to have a diameter that is similar to or slightly less than the diameter of the channels 36, 38 (in order to allow for clearance between the rods 56, 58 and the channels 36, 38). In one embodiment, the first channel 36 and the second channel 38 are open channels such that at least a portion of the first rod 56 and the second rod 58 is visibly exposed through the exterior surface 30 of the shaft 22 (FIG. 2B) when the instrument 20 is assembled.

In one embodiment, the rods 56, 58 are flexible and pre-flexed or stressed such that the distal ends 52 deflect inwardly toward each other as illustrated by the distance H2 in FIG. 3C showing the distal ends 52 are more narrowly spaced apart than the distance H1 between the rods 56, 58 near the handle 60 (FIG. 3B). In particular, in one embodiment the rods 56, 58 are spaced by the first distance H1 apart near the handle 60 as illustrated in the cross-sectional view of the proximal end portion of FIG. 3B and the distal ends 52 of the rods 56, 58 are tensioned (e.g., bent) to flex together such they are spaced apart by a distance H2 that is less than the distance H1 as illustrated in the cross-sectional view of the distal end portion of FIG. 3C. In this manner, when the rods 56, 58 are engaged with the channels 36, 38 (FIG. 2B) the shaft 22 maintains the rods 56, 58 apart, one from the other, by the distance H1. Alternatively, when the distal ends 52 of the rods 56, 58 extend beyond the distal end 32 of the shaft 22 (FIG. 2A) the ends 52 are unconstrained and thus flex and pinch together a distance H2 apart.

Figure 9:
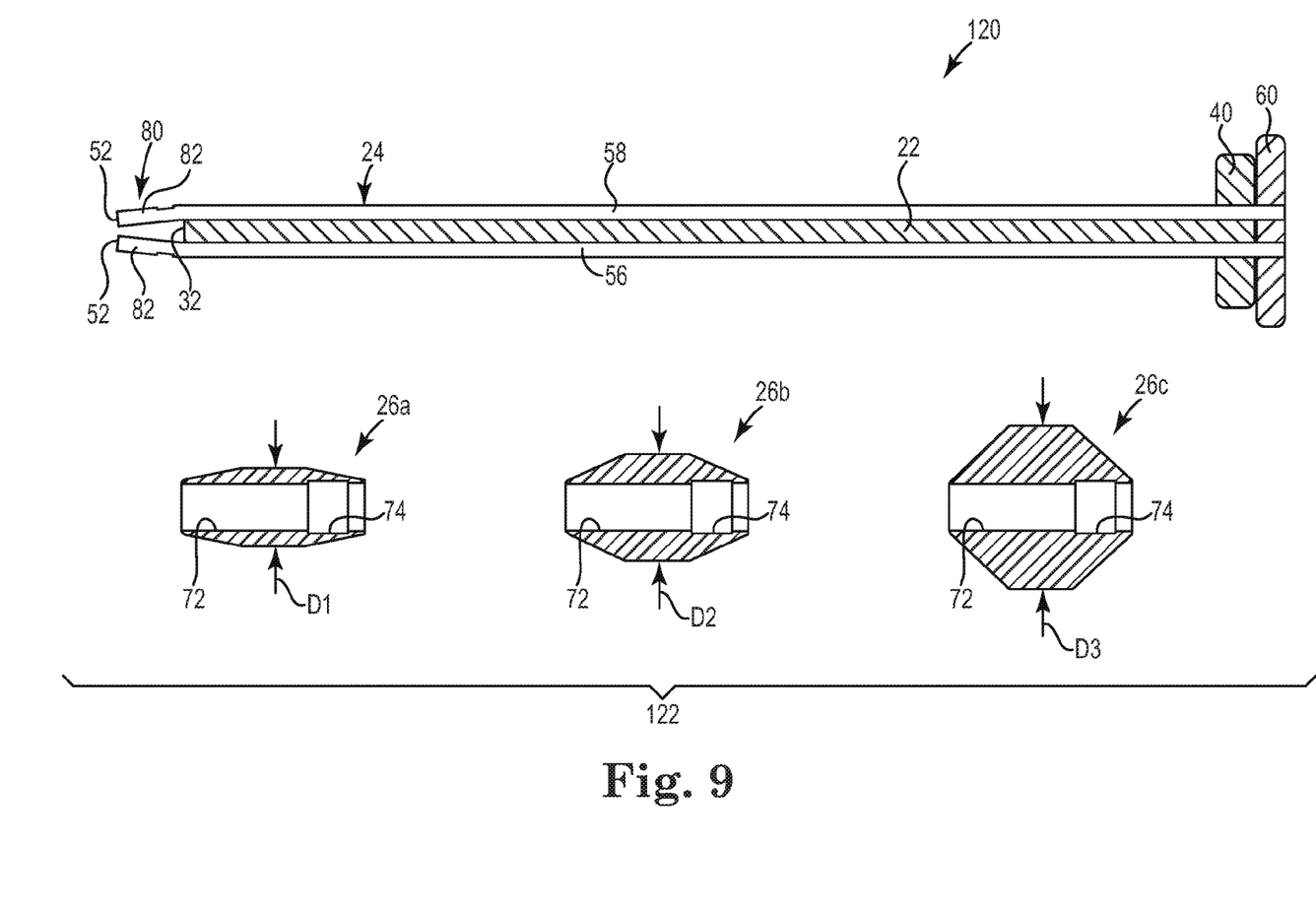
FIG. 9 is a cross-sectional view of one embodiment of an instrument system that is configured to measure and dilate an opening in a penis.

In one embodiment, the rods 56, 58 are formed to be substantially parallel with each other, for example as illustrated by the rods of plunger 134 in FIG. 9.

Figure 4A:
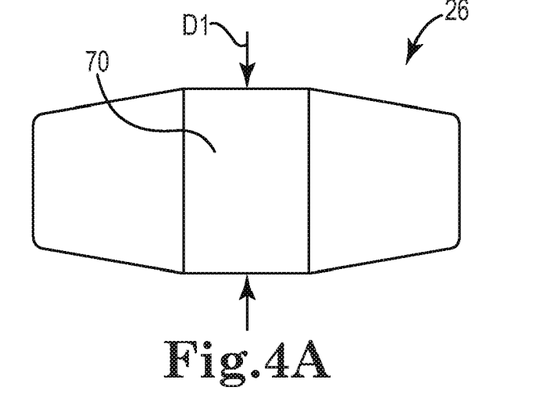
FIG. 4A is a side view of one embodiment of a dilation head that is attachable to the plunger illustrated in FIG. 3A.
Figure 4B:
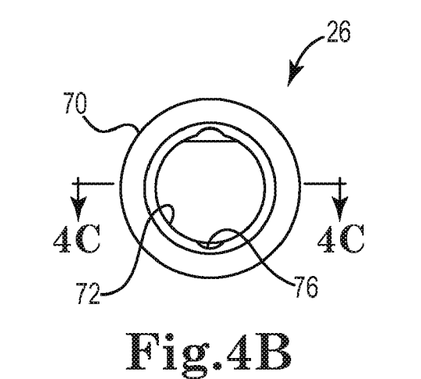
FIG. 4B is an end view of the dilation head illustrated in FIG. 4A.
Figure 4C:
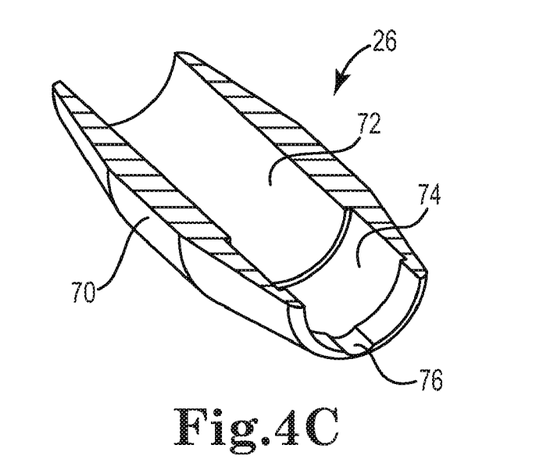
FIG. 4C is a cross-sectional view of the dilation head illustrated in FIG. 4B.

FIG. 4A is a side view, FIG. 4B is an end view, and FIG. 4C is a cross-sectional view of the dilation head 26. In one embodiment, the dilation head 26 includes an exterior surface 70 having an outside diameter of D1 and an inside surface 72 that is formed to provide a recess 74. The dilation head 26 is attachable to the distal ends 52 of the rods 56, 58 and its annular conformation is configured to be disposed over the shaft 22. In one embodiment, the recess 74 is provided as an annular groove formed around the inside surface 72 of the dilation head 26.

In one embodiment, the diameter D1 is larger than the diameter of the shaft 22 (FIG. 2B) and the inside surface 72 of the dilation head 26 includes clearance notches 76 sized to move over the rods 56, 58 (FIG. 3B) of the assembled instrument 20. In one embodiment, the dilation head 26 is removably attachable and re-attachable to the plunger 24 (FIG. 3A). Suitable examples of mechanisms that allow the dilation head to be removed from the plunger 24 include tension latches, threads, snap fits, friction fits, and quarter-turn quick attachment mechanisms (e.g., post-and-slot arrangements).

In one embodiment, the instrument 20 is configured to be reusable and is fabricated from a suitable material such as a polymer. Suitable polymers include polysulfone, polyetherimide, or polyester, or blends or derivatives of polysulfone, polyetherimide, or polyester. In one example, the shaft 22, the plunger 24, and the dilation head 26 are each fabricated from polysulfone and thus configured for disposable single surgical use.

Figure 5A:
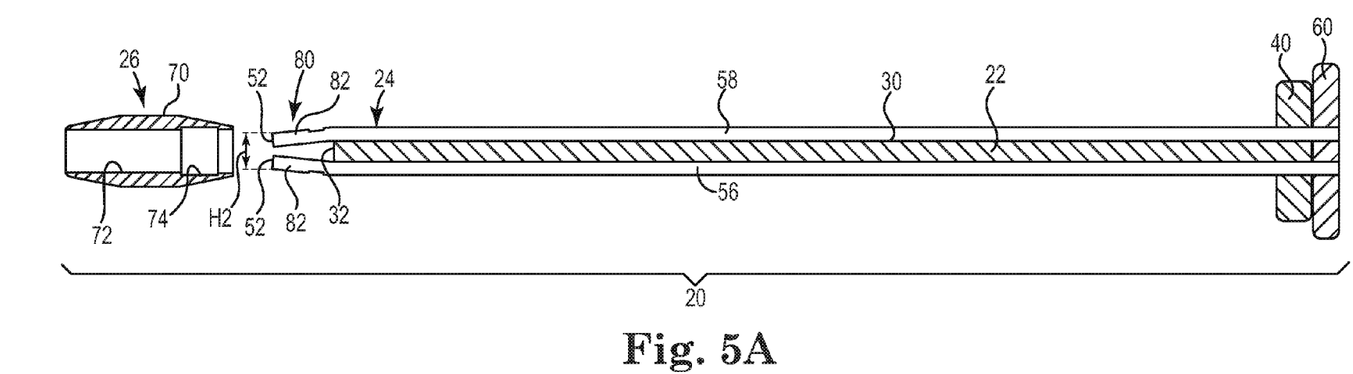
FIG. 5A is a cross-sectional view of the instrument illustrated in FIG. 1.

FIG. 5A is a cross-sectional view of the dilation head 26 disengaged from the plunger 24. In one embodiment, the plunger 24 is longer than the shaft 22 such that the distal ends 52 of the rods 56, 58 extend beyond the distal end 32 of the shaft 22 when the handle 60 of the plunger 24 is in contact with a handle 40 of the shaft 22. In one embodiment, the distal ends 52 of the rods 56, 58 combine to provide a tension latch 80. The tension latch 80 is flexible and compresses to release from the dilation head 26 (FIG. 5A) and expands to engage with the dilation at 26 (FIG. 5B).

For example, in one embodiment the tension latch 80 includes a boss 82 that extends from an exterior surface of the each of the rods 56, 58. The tension latch 80 is characterized in that the distal ends 52 of the rods 56, 58 deflect inwardly together when the ends 52 of the plunger 24 extend beyond the shaft 22, which provides clearance for the bosses 82 to pass inside the interior surface 72 of the dilation at 26 for attachment/removal of head 26 from plunger 24. For example, and with additional reference to FIG. 3C, the distal ends 52 of the rods 56, 58 deflect inwardly to a spacing of approximately H2, which provides clearance for the bosses 82 to enter inside the interior surface 72 of the dilation head 26. That is to say, the inside diameter of the inside surface 72 is about equal to the distance H1 plus twice the diameter of one of the proximal portion of the rods 56, 58.

Figure 5B:
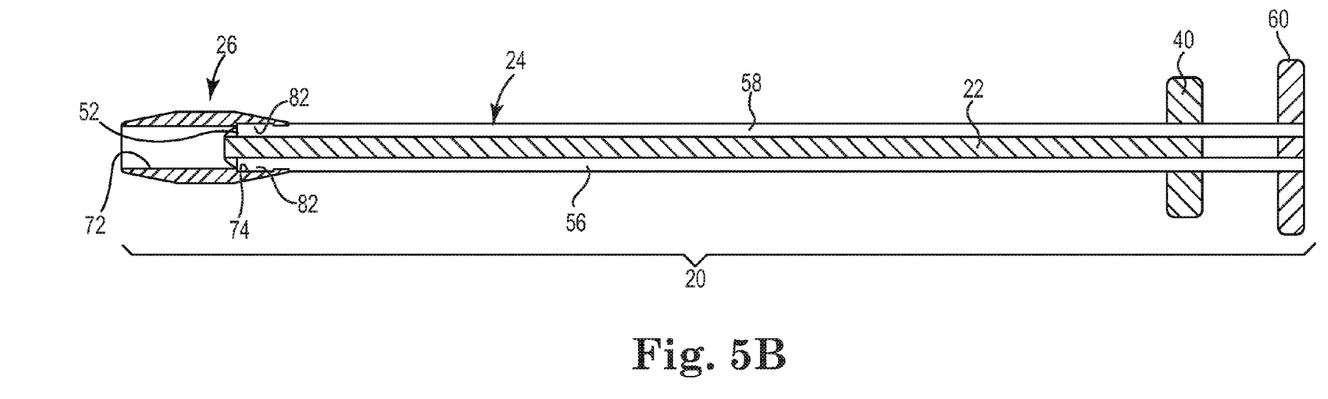
FIG. 5B is a cross-sectional view of the instrument illustrated in FIG. 5A with the dilation head coupled to a distal end of the plunger.

FIG. 5B is a cross-sectional view of the dilation head 26 attached to and engaged with the Plunger 24. When the dilation head 26 is placed over the compressed distal ends 52 of the rods 56, 58 (FIG. 5A) and the plunger 24 is retracted such that the ends 52 no longer extend beyond the shaft 22, then the bosses 82 of the tension latch 80 are forced outward to engage with the recess 74 of the dilation head 26. In this manner, a removable dilation head 26 is provided for the instrument 20, which allows the surgeon to select differently sized dilation heads 26 to selectively dilate the corpora of the penis to a desired diameter, as described below.

The plunger 24 is movable longitudinally relative to the shaft 22. Movement of the plunger 24 back and forth relative to the shaft 22 moves the dilation head 26 longitudinally back and forth along the shaft 22. In one embodiment, the handle 40 attached to the shaft 22 is separated from the handle 60 attached to the plunger 24 when the distal ends 52 of the plunger 24 are located between the distal end 32 and a proximal end 30 of the shaft 22.

Figure 6:
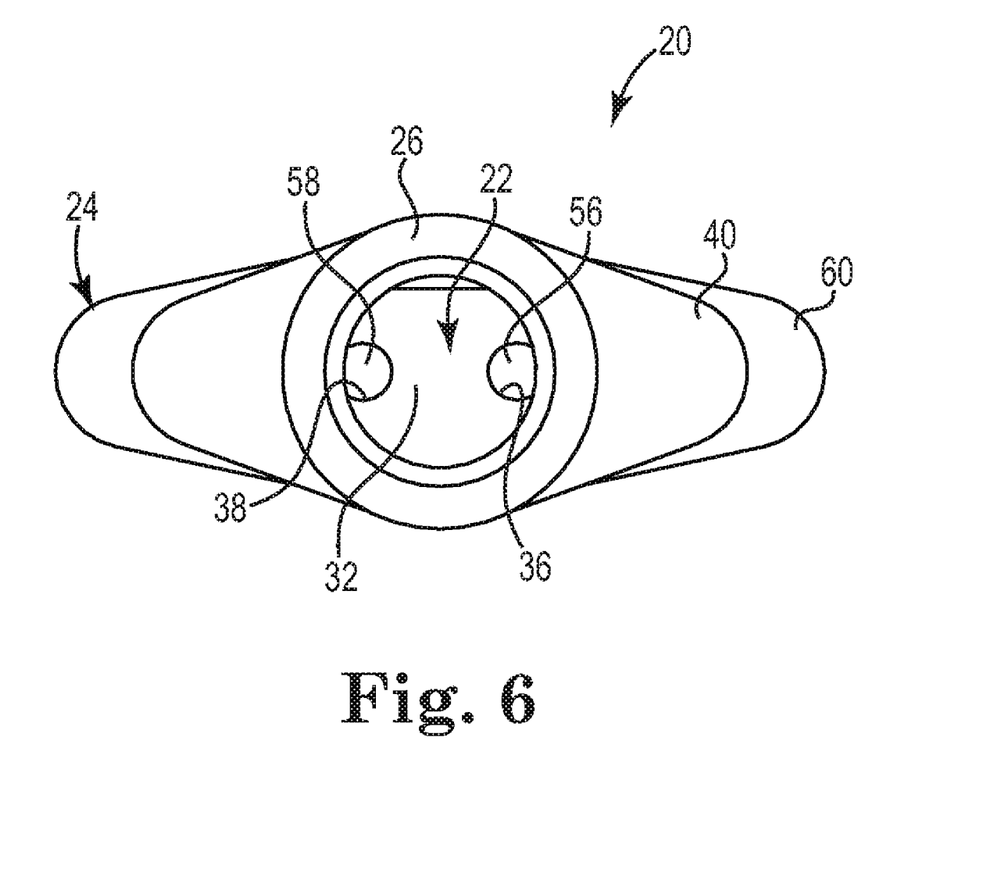
FIG. 6 is an end view of the instrument illustrated in FIG. 5B.

FIG. 6 is an end view of the instrument 20. The plunger 24 is engaged with the shaft and 22 such that the rods 56, 58 are engaged with the channels 36, 38 formed in the shaft 22. The dilation head 26 is attached to the rods 56, 58 of the plunger 24 such that the dilation head 26 is disposed around the shaft 22.

Figure 7A:
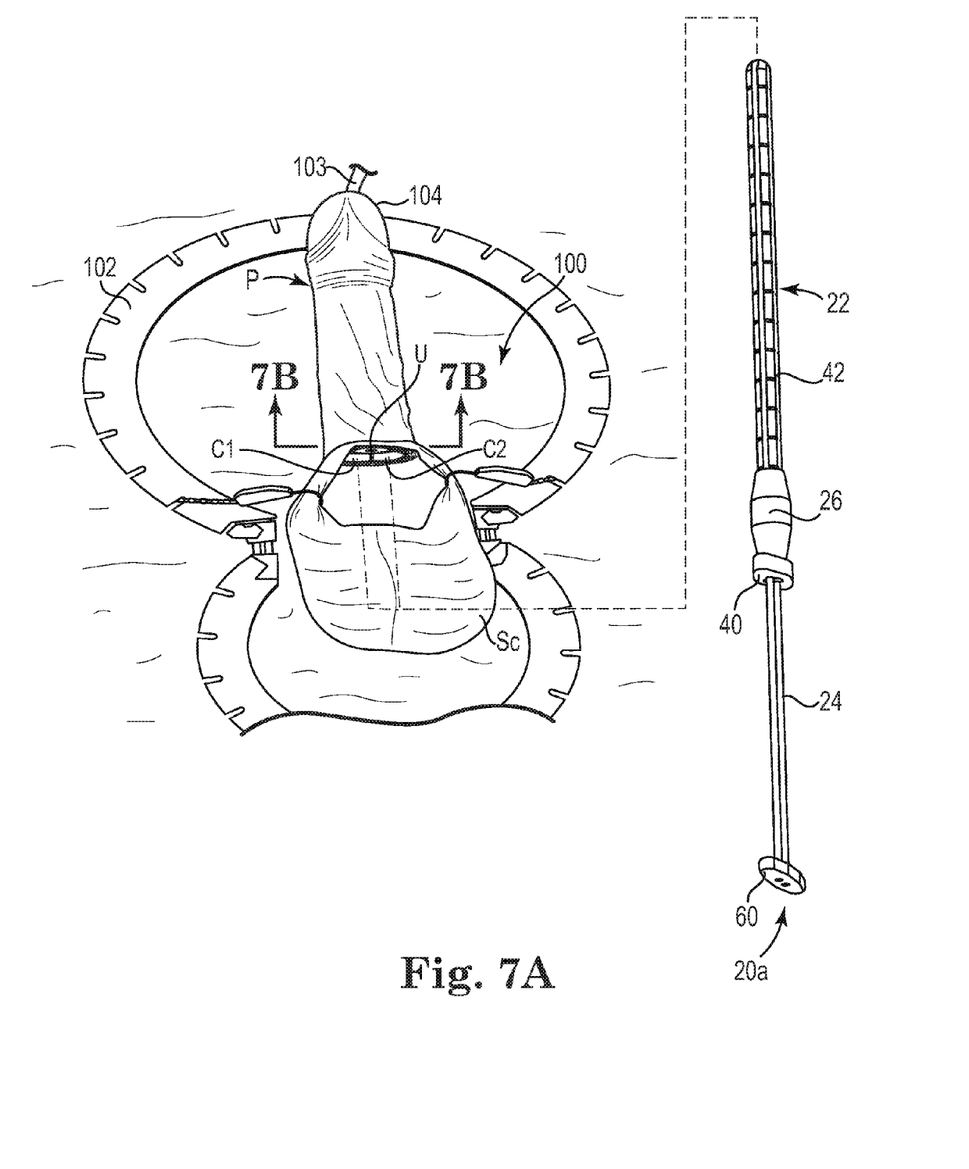
FIG. 7A is a schematic view of one embodiment of a penis prepared for implantation of a penile prosthetic showing the instrument in a corpora measurement configuration and FIG. 7B is a cross-sectional view of the corpora of the penis.
Figure 7B:
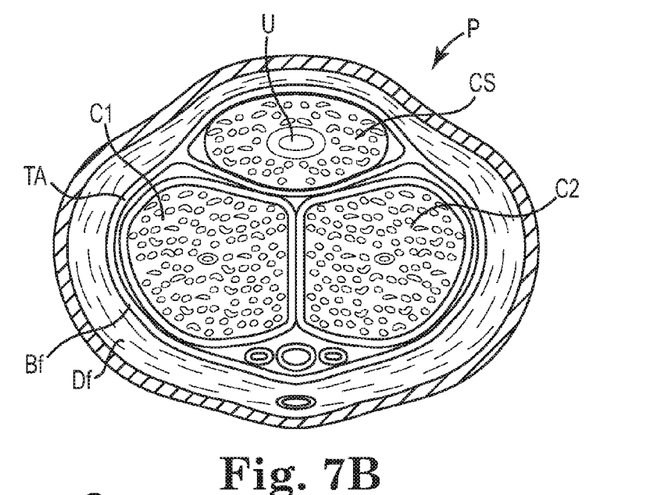

FIG. 7A is a schematic view of one embodiment of a penis P prepared for implantation of a penile prosthetic showing the instrument 20a in a corpora measurement configuration and FIG. 78 is a cross-sectional view of the corpora C1 and C2 of the penis P. While the penile prosthetic is not shown, it would typically include a pair of inflatable cylinders, a reservoir, and a pump employed to transfer fluid to/from the reservoir, where the instrument 20 is employed to dilate the corpora for insertion of the cylinders.

The penis P is reclined against the torso such that the urethra U, surrounded by corpus spongiosum tissue, is oriented upward. The penis P has been incised to expose the corpora cavernosa (C1 and C2) and the instrument 20a has the dilation head 26 fully retracted proximally to allow the shaft 22 to measure the length of each of the corpora cavernosum (C1 or C2). In the corpora measurement configuration, the entire distal portion of the shaft 22 is unobstructed from the dilation head 26.

The groin area 100 of the patient is shaved, cleaned and suitably prepped with a surgical solution prior to draping with a sterile drape as directed by the healthcare provider's procedures. A retraction device, such as a retractor 102 sold under the trademark Lone Star and available from Lone Star Medical Products of Stafford, Tex., is placed around the penis P if so desired by the surgeon to establish a surgically clean field. A catheter 103 is inserted into the urethra U from the distal end 104 of the penis P. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, with reference to FIG. 7B, the surgeon forms a 2-3 cm transverse incision through the subcutaneous tissue of the median raphe of the upper scrotum Sc and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

With reference to both FIGS. 7A and 7B, the surgeon typically will insert a blunt-ended scissors or other elongated tool to separate a portion of the spongiosum material to open a pathway, for the instrument 20a. The surgeon inserts the shaft 22 (instrument 20a) into the corpora cavernosa C1 and C2 to measure the proximal and distal length of each corpora cavernosum C1 and C2. For example, the shaft 22 is inserted into one of the corpora cavernosa C1 or C2 forward in the distal penis toward the glans penis, the distal measurement is recorded by reading the indicia 42, and the shaft 22 is inserted into the same corpora cavernosa C1 or C2 rearward in the proximal penis toward the crus of the penis to record the proximal length of the corpora by reading the indicia 42. The distal and proximal measurements would typically be made in reference to a "stay stitch" temporarily placed in the incision. The sum of the distal and the proximal measurements represent the length of the corpora into which the implant is placed. This procedure is repeated for the other of the corpora cavernosa C1 or C2 to measure the length of the companion corpora. Thereafter, each corpora cavernosum C1 and C2 is dilated distally and proximally with the instrument 20.

Figure 8A:
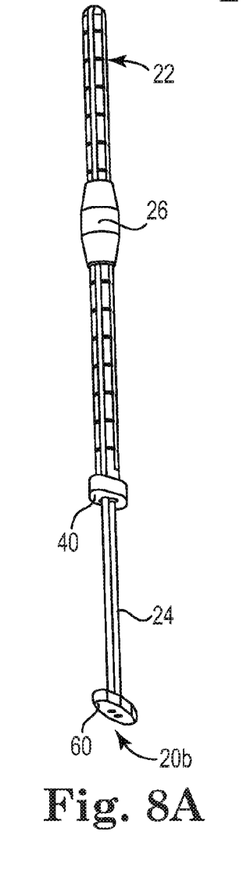
FIGS. 8A and 8B illustrate the instrument in dilation configurations with the dilation head moved to different locations along the shaft.
Figure 8B:
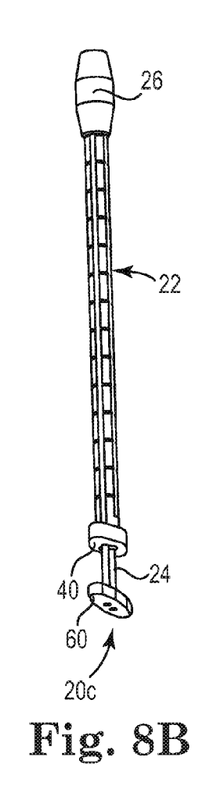

FIGS. 8A and 8B illustrate the instrument 20 in the dilation configurations with the dilation head 26 moved midway along the shaft 22 (FIG. 8A) and the dilation head 26 moved to the distal end of the shaft (FIG. 8B). In one exemplary approach, the surgeon begins dilation of the distal and proximal corpora cavernosum C1 and C2 by introducing a dilation head 26 having an 8 mm outside diameter (D1 in FIG. 4A) into the spongy tissue of one of the corpora C1 or C2. The plunger 24 is moved into the shaft 22 to move the dilation head 26 from a proximal location (instrument 20a in FIG. 7A) to a distal location (instrument 20c) to open the spongy tissue of the corpora along the length of the penis P. The plunger 24 is withdrawn proximally with the shaft 22 remaining in the penis P, and if the surgeon determines it to be desirable, once again advances the dilation head 26 distally and longitudinally along the shaft 22 to fully dilate the tissue of the corpora. Thereafter, the surgeon may optionally remove the instrument 20 from the penis P, remove the 8 mm dilation head, for example, and attach a larger diameter dilation head 26 to the plunger 24, and insert the newly configured tool 20 into the penis P to sequentially dilate the corpora cavernosum C1 and C2 to a width that accommodates the selected cylinder diameter of the implant.

In another exemplary approach, the surgeon may choose to dilate the distal and proximal corpora by a single introduction of a dilation head having a 14 mm outside diameter. Alternatively, the surgeon may choose to sequentially dilate the corpora with a series of dilation heads 26 having an outside diameter ranging from 8 mm to 10 mm to 12 mm and outward to 14 mm in diameter, in the manner described above. Other dilation heads 26 wider than 14 mm are also within the scope of this disclosure. In any regard, the dilation head 26 is introduced and pushed distally toward the glans penis and proximally toward the crus of the penis to dilate each of the corpora cavernosum C1 and C2 along its length. After dilation of the corpora cavernosum C1 and C2, the surgeon selects a proper length of implant and proceeds with placement of cylinders of the implant within the fully dilated corpora.

FIG. 9 is a cross-sectional view of an instrument system 120 including a set 122 of dilation heads 26, each removably attachable to the tension latch 80 of the plunger 24. In one embodiment, the set 122 of dilation heads includes multiple dilation heads 26a, 26b, 26c each having a different diameter, where each dilation head 26a, 26b, 26c is configured to couple to the distal ends 52 of the plunger 24. In one embodiment, the instrument 20 (FIG. 1) and the set 122 of dilation heads are provided as a kit of parts.

In one embodiment, dilation head 26a is provided with an outside diameter D1, dilation head 26b is provided with an outside diameter D2, and dilation head 26c is provided with an outside diameter D3, where D3 is greater than D2, and D2 is greater than D1. As an example, in one embodiment the diameter D1 is about 8 mm, the diameter D2 is about 10 mm, and a diameter D3 is about 12 mm. It is to be understood that the set 122 of dilation heads 26 could be provided with diameters ranging from 6 mm to 18 mm or more, in increments of about 2 mm, for example, depending upon the patient size or surgeon preference.

Each of the dilation heads 26a, 26b, 26c is provided with a recess 74 that is configured to couple with the bosses 82 of the tension latch 80. During use, the surgeon would initially measure the length of the corpora cavernosa C1 and C2 with the shaft 22, dilate the distal and proximal corpora cavernosa C1 and C2 (FIG. 7B) in the range of D1 with the dilation head 26a, remove the dilation head 26a and attach the larger diameter D2 of the dilation head 26b to the plunger 24, dilate the distal and proximal corpora cavernosa C1 and C2 in the range of D2, and remove the dilation head 26b and attach the even larger diameter of the dilation head 26c to the plunger 24 to sequentially and fully dilate the distal and proximal corpora cavernosa C1 and C2 of the penis P in the range of D3.

Figure 10:
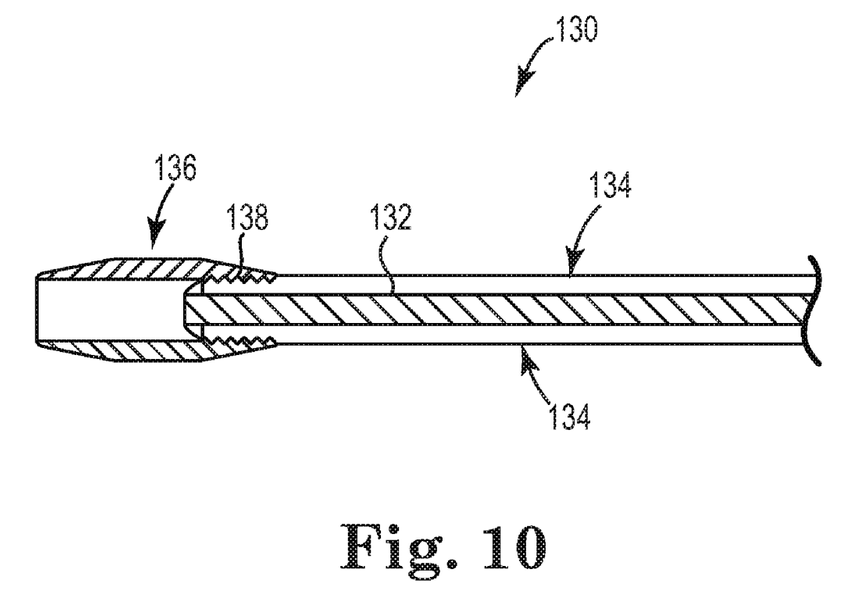
FIG. 10 is a cross-sectional view of one embodiment of an instrument including a dilation head threaded onto a distal end of a plunger.

FIG. 10 is a cross-sectional view of one embodiment of an instrument 130 that is configured to prepare a penis for implantation of a penile prosthetic and including a dilation head 136 threaded onto a distal end of a plunger 134. The instrument 130 includes a shaft 132 that supports the plunger 134 in a manner similar to that described above for instrument 20. In one embodiment, the distal end of the plunger 134 is threaded to receive threads formed on an inside surface of the dilation head 136. In this manner, the dilation head 136 is removable from the distal end of the plunger 134 in a twist-on and twist-off approach. As described above in FIG. 8, one embodiment of instrument 130 includes a set of dilation heads, where each dilation head is removably attachable to the plunger 134 to allow the surgeon to sequentially dilate the corpora cavernosa to an increasingly larger diameter.

Embodiments provide an instrument that is configured to prepare a penis for implantation of a penile prosthetic, where the instrument includes a shaft suited for measuring a length of the corpora cavernosum and a dilation head that is movable longitudinally along the shaft of the instrument to dilate the corpora cavernosum. Thus, a single instrument is provided that has improved cost effectiveness and procedural efficiency over the prior tools, and is suited to measure and dilate the corpora cavernosum of the penis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An instrument configured to prepare a penis for implantation of a penile prosthetic, the instrument comprising:
   a shaft extending between a distal end and a proximal end;
   a plunger coupled to and movable relative to the shaft; and
   a dilation head coupled to a distal end of the plunger and disposed around an exterior of the shaft, the dilation head movable longitudinally along the shaft,
   wherein the plunger comprises a first rod and a second rod and an exterior surface of the shaft defines a first channel sized to receive the first rod and a second channel sized to receive the second rod.

2. The instrument of claim 1, wherein the first channel and the second channel are open channels such that at least a portion of the first rod and the second rod is exposed through the exterior surface of the shaft.

3. The instrument of claim 1, wherein the first channel is spaced a first distance from the second channel such that the first and second rods are spaced apart by the first distance when engaged in a respective one of the first and second channels.

4. The instrument of claim 3, wherein distal ends of the first and second rods flex laterally such that each is spaced apart from the other by a distance that is less than the first distance when the distal end of the plunger is moved past the distal end of the shaft.

5. The instrument of claim 4, wherein the distal ends of the first and second rods provide a tension latch, the tension latch engaged with the dilation head when the distal end of the plunger is between the distal end and the proximal end of the shaft and the tension latch disengaged with the dilation head when the distal end of the plunger is moved past the distal end of the shaft.

6. The instrument of claim 1, wherein the plunger is longer than the shaft and the dilation head is removably coupled to a distal end of the plunger.

7. The instrument of claim 6, further comprising:
   a first handle attached to the proximal end of the shaft; and
   a second handle attached to a proximal end of the plunger.

8. The instrument of claim 7, wherein the first handle is separated from the second handle when the distal end of the plunger is between the distal end and the proximal end of the shaft and the first handle contacts the second handle when the distal end of the plunger is moved past the distal end of the shaft.

9. The instrument of claim 1, wherein the dilation head is reversibly movable longitudinally between the distal end of the shaft and the proximal end of the shaft.

10. The instrument of claim 1, wherein an exterior surface of the shaft comprises measurement indicia.

11. The instrument of claim 1, wherein the shaft has an outside diameter and the dilation head has a first diameter that is greater than the outside diameter of the shaft.

12. The instrument of claim 1, wherein the shaft has a constant outside diameter.

13. The instrument of claim 1, wherein the dilation head is a first dilation head that is removable from the plunger and replaceable with a second dilation head having a second diameter that is different from the first diameter of the first dilation head.

14. An instrument system configured to prepare a penis for reception of a penile prosthetic, the instrument system comprising:
- a longitudinal shaft having a constant outside diameter configured to measure the opening in a penis;
- a plunger coupled to and movable longitudinally within the shaft; and
- a set of dilation heads, each dilation head configured to couple to a distal end of the plunger, surround an exterior of the shaft, and move longitudinally along the shaft;
- wherein each dilation head in the set of dilation heads has a different outside diameter
- wherein the plunger comprises two longitudinally disposed rods that are separated laterally apart by the shaft to apply engagement tension to each dilation head coupled to the distal end of the plunger.

15. The instrument system of claim 14, wherein each rod comprises a boss that projects from an exterior surface of the rod, and each dilation head includes a recess formed on an interior surface of the dilation head, the boss configured to couple with the recess.

16. The instrument system of claim 15, wherein the rods are movable laterally to disengage the boss from the recess.

17. The instrument system of claim 16, wherein the plunger is longer than the shaft such that the rods move laterally together when a distal end of the plunger extends over a distal end of the shaft.

* * * * *